United States Patent [19]

Jain

[11] 4,441,978
[45] Apr. 10, 1984

[54] SEPARATION OF PROTEINS USING ELECTRODIALYSIS - ISOELECTRIC FOCUSING COMBINATION

[75] Inventor: Surendar M. Jain, Watertown, Mass.

[73] Assignee: Ionics Incorporated, Watertown, Mass.

[21] Appl. No.: 466,821

[22] Filed: Feb. 16, 1983

Related U.S. Application Data

[62] Division of Ser. No. 278,267, Jun. 29, 1981, Pat. No. 4,396,477.

[51] Int. Cl.³ .............................................. B01D 13/02
[52] U.S. Cl. ................................. 204/301; 204/180 P; 204/180 R; 204/299 R
[58] Field of Search ............... 204/301, 299 R, 180 P, 204/180 R

[56] References Cited

U.S. PATENT DOCUMENTS

| | | | |
|---|---|---|---|
| 2,694,680 | 11/1954 | Katz et al. | 204/301 |
| 4,204,929 | 5/1980 | Bier | 204/301 |
| 4,276,140 | 6/1981 | Jain | 204/301 |

Primary Examiner—John F. Niebling
Assistant Examiner—B. J. Boggs, Jr.
Attorney, Agent, or Firm—Norman E. Saliba

[57] ABSTRACT

A process and apparatus for treating a liquid protein mixture is disclosed in which the protein mixture is first demineralized by electrodialysis (ED) and then subjected to isoelectric focusing (IEF) to effect the separation of proteins based on differences in their isoelectric points (pI). This combination of ED-IEF results in an improved separation of the protein components of a mixture than without the ED step.

4 Claims, 2 Drawing Figures

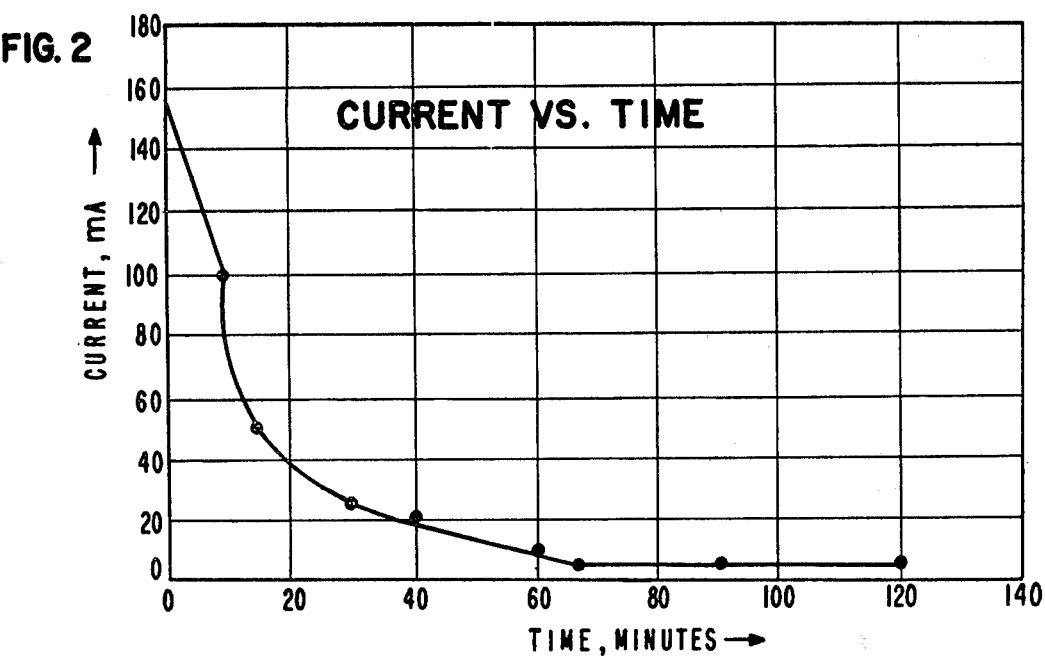
FIG. 2
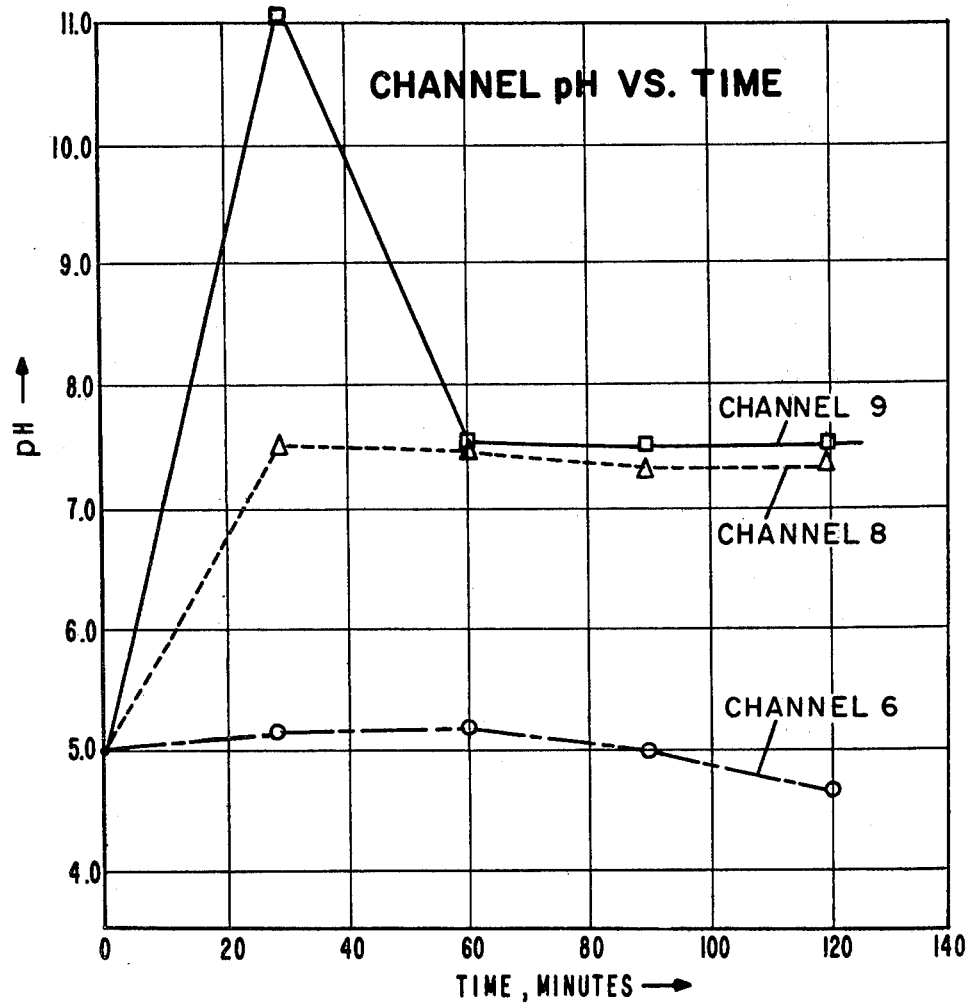

SEPARATION OF PROTEINS USING ELECTRODIALYSIS - ISOELECTRIC FOCUSING COMBINATION

This application is a division of application of Ser. No. 278,267, filed June 29, 1981, now U.S. Pat. No. 4,396,477.

FIELD OF THE INVENTION

The invention deals with the separation of protein mixtures by a novel combination of electrodialysis and electrofocusing. The use of electrodialysis prior to electrofocusing makes the process more efficient and improves the quality of the recovered proteins.

DESCRIPTION OF THE PRIOR ART

The two separate techniques of isoelectric focusing and electrodialysis are by themselves well known in the art. Isoelectric focusing is used to focus proteins according to their isoelectric point which is the pH at which the negative and positive charges of a particular protein are equal. On reaching this pI, the proteins become immobile in an electric field. Isoelectric focusing methods of the recirculating type are described in U.S. Pat. Nos. 4,204,929 (Bier), 4,217,193, 4,243,507 (Martin, et al), and others. U.S. Pat. No. 4,130,470 (Rosengren, et al) describes another method for carrying out IEF without the use of carrier ampholytes. All of the above-mentioned patents are incorporated herein by references. A detailed discussion of the subject is given by Righetti & Drysdale in "Laboratory Techniques in Biochemistry and Molecular Biology", American Elsevier Publishing Co., Inc., New York (1976) and by N. Catsimpoolas (Ed.) of "Isoelectric Focusing", Academic Press, New York (1976).

These techniques and other prior art methods aim at obtaining bands of pure materials focused according to the pI's. The pH gradients have a tendency to vary with time and a flow distortion of the pH gradient results in a movement of the sample zone. One of the major factors causing these disturbances is the presence of dissolved salts in the samples. The presence of excess salt will also cause the generation of excess heat, and will further impede the transfer of sample substances to their pI since the salt carries the current preferentially. In such separation, the application of a higher voltage will help to speed up the process but the presence of salt does not readily allow this to take place. Presently the samples to be electrofocused are first dialyzed to decrease the salt level. However, with dialysis the salt level is difficult to control and solutions in which proteins precipitate out are difficult to handle.

Still in other cases, certain proteins have a tendency to precipitate out in the IEF apparatus during the course of operation. By use of controlled desalting of the protein mixture (with or without pH adjustment) one can pre-precipitate the impurities during the course of the electrodialysis and thereby obviate the difficulty of separation in the subsequent IEF step.

It has now been found that many of the above-mentioned difficulties can be overcome by first removing the salt by electrodialysis in a controlled fashion to any concentration desired and thereafter employing the isoelectric focusing technique.

DESCRIPTION OF THE DRAWINGS

FIG. 2 illustrates current and channel pH variation with time for an IEF experiment with electrodialyzed albumin-hemoglobin mixture described in Example 2.

DESCRIPTION OF THE PREFERRED EMBODIMENT

Figure 1:
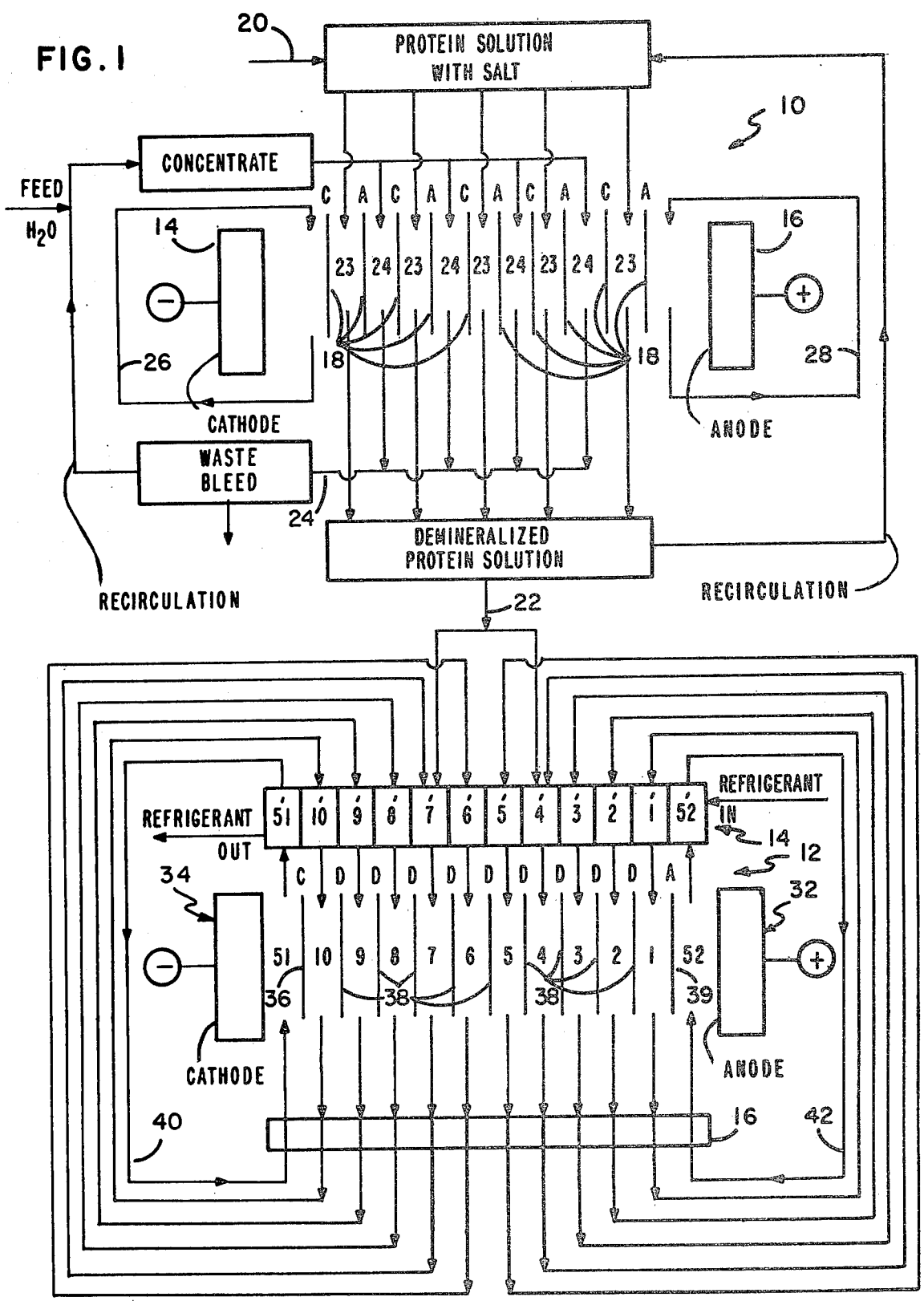
FIG. 1 illustrates a schematic cross-sectional representation of the combination apparatus used in the process of the invention.

Referring to FIG. 1, there is shown in schematic representation an electrodialysis cell 10 and an isoelectric focusing cell 12. Each cell is composed of a cathode, an anode, and a plurality of separating membranes. In the electrodialysis cell 10, cathode 14, anode 16 and ion permselective membranes 18 function to separate the salts from the protein mixture entering the stream 20. The protein mixture passes through desalting chambers 23 defined between alternating cation membranes, C, and anion membranes, A, held and separated in a stack arrangement by means not shown but well known in the prior art. Tortuous path spacer compartments of the type disclosed in U.S. Pat. Nos. 2,708,658 and 2,891,899 can be employed to separate the membranes from each other to form alternating desalting and concentrating chambers or compartments. The combination of a desalting and concentrating chamber constitutes a cell pair. Any number of cell pairs can be stacked between a pair of end electrodes to produce a demineralization stack containing typically 100 cell pairs or more. Such systems are more fully described in U.S. Pat. Nos. 2,694,680, 2,752,306, 2,848,403, 2,891,899, 3,003,940, 3,341,441, and 3,412,006. The manufacture and properties of ion-selective membranes of the type employed in the electrodialysis systems are fully discussed in U.S. Pat. No. Re. 24,865, U.S. Pat. Nos. 2,730,768, 2,702,272, 2,731,411 and many others. Under the influence of the electrical potential across the cell, positively charged ions such as sodium and potassium migrate through cation membranes C into waste compartments or concentrate (brine) stream 24. Similarly, negatively charged ions such as chloride pass through anion membranes A into the waste or salt concentrating stream. Although the above-mentioned ions comprise the main body of the salts, other ionic substances are or may also be removed in a like manner. Additionally, in the operation of the electrodialysis cell, a recirculating electrolyte stream 26 is passed in contact with the cathode and a similar stream 28 in conact with the anode. Demineralized protein solution collected from stream 22 may now be introduced into one or several channels of a heat exchanger reservoir 14 either by a pump or by gravity and then to a isoelectric focusing (IEF) cell 12. Such a cell has been described in detail in U.S. Pat. No. 4,204,929 (Bier). It consists of a stack of substantially flat parallel spacers made of a non-conductive material having a control aperture for feeding the liquid in and out. Adjacent pairs of spacers are separated by permeable membranes 38. These membranes can be with or without a frame. Thus, a number of channels designated by reference numerals 1, 2, 3, 4 . . . 9, 10 are created by these membranes. There are also two extra channels 51 and 52 at the ends of the stack separated by a cation permeable membrane 36 and an anion permeable membrane 39 respectively. The channels may optionally contain a screen or some open plastic material to support the permeable membranes. This stack of spacers and membranes is placed between a cathode 34 and an anode 32 and the assembly is then clamped together by a pair of end plates (not shown). The end channels 51 and 52 are fed with electrode buffer solutions 40 and 42. A power supply (not shown) is connected to the cathode and anode to supply a direct electric current across the stack.

The heat exchanger reservoir 14 has also channels indicated by numerals 1́, 2́, 3́ ... 9́, 1́0, 5́1, 5́2 corresponding to the channels 1, 2, 3 ... 9, 10, 51, 52 of the isoelectric focusing cell 12. Each of the channels is pumped by a multichannel pump 16 to the corresponding channel of the exchanger reservoir 14, i.e., channel 1 into 1́; 2 into 2́, etc. The electrode channels 51 and 52 are pumped into the cell rather than gravity feeding to facilitate gas removal during operation.

Although the focusing cell and heat exchanger reservoir have been shown with twelve channels, it is merely for illustrative purposes; this number can be more or less and not limited to twelve.

The fluid entering or exiting each of the channels can be monitored for pH, temperature, conductivity, concentration, etc. by an appropriate monitor placed within the reservoir channels or in the lines leading to or exiting therefrom.

In FIG. 1, the electrodialyzed protein mixture 22 is shown gravity fed to the isoelectric focusing cell 12 and the return of this mixture by means of the pump 16. Several other modes of feeding can be incorporated as described in U.S. Pat. No. 4,204,929 depending upon the situation, e.g. one may wish to pump the fluid into the IEF apparatus and return the fluid by gravity or have separate pumps to both feed and withdraw the fluid from the apparatus. The recycling mode may also be replaced by a single pass continuous flow operation.

The IEF cell is generally operated with the prior establishment of a pH gradient (or function) by focusing of ampholytes such as those obtained from LKB Produkten of Sweden under the trademark Ampholine. The demineralized protein solution may be mixed with ampholytes or other suitable buffer systems described in a paper entitled "New Developments in Isoelectric Focusing" by M. Bier, et al in Proceedings of the Sixth American Peptide Symposium, Pierce Chemical Co. (1979). In some other cases, these buffers and ampholytes may not be needed and the protein mixture may be electrofocused directly. Still in another case, the pH function may be generated by having chargeable groups immobilized on or into the permeable membranes to vary the pH function in channels, e.g. 1, 2–9, 10, etc. by having chemically affixed groups of various concentrations thereby preventing the transport of these groups upon application of electric field as fully described in U.S. Pat. No. 4,130,470 (Rosengren, et al). Or still in another case, the charges may be immobilized on the support screen. Such a system obviates the necessity of prefocusing or mixing which is required in cases where ampholytes are used and hence shortens the time required to focus a sample.

The choice of introducing the demineralized protein solution 22 into a particular channel or channels is dictated by the pI of the protein of interest, it being preferable to introduce the mixture into the channels of pI's closer to the protein of interest since the separation is faster with such a method of introduction of sample giving a higher throughput.

The following examples will show the efficacy of using electrodialysis prior to using the isoelectric focusing apparatus.

EXAMPLE 1

In this example 235 ml of a protein mixture containing Cohn Fraction V having 96% pure albumin (pI~4.9) and hemoglobin (pI~7.4) was used each at a 0.7 wt./vol. percent. The salt content of this mixture approximated the isotonic level, i.e., 0.15 N NaCl and a conductivity of 11.35 mS (milliSiemens) at 25° C. No ampholytes were added to this mixture. The electrolyte buffers used for the cathode stream was 80 ml 0.1 M NaOH and for the anode stream it was 80 ml 0.1 M $H_3PO_4$.

A 10 channel IEF apparatus was used and operated in the recycling mode as illustrated in FIG. 1 and in U.S. Pat. No. 4,204,929 (Bier). The power supply employed had an upper limit of 250 ma and the ability to be operated in a constant power mode. Initially the current was set at the highest value of 250 ma. When the current started dropping the power supply was set in a constant power mode of 50 watts. During this time the voltage started increasing to keep the current as high as possible. The following Table I summarized the results on three channels.

TABLE I

| Time Min. | Current M amp. | pH in Efficient Channels | | | Relative Protein Concentration in Channels | | |
|---|---|---|---|---|---|---|---|
| | | 6 | 8 | 9 | 6 | 8 | 9 |
| 0 | 250 | 5.0 | 5.0 | 5.1 | 10.5 | 10.5 | 10.5 |
| 60 | 250 | 5.1 | 11.8 | 12.0 | 11.1 | 12.6 | 14.1 |
| 90 | 250 | 11.1 | 12.1 | 12.1 | 12.5 | 12.6 | 14.0 |
| 150 | 200 | 11.9 | 12.2 | 12.1 | 20.0 | 15.1 | 10.1 |
| 210 | 180 | 12.2 | 12.2 | 12.1 | 17.9 | 14.6 | 7.4 |

It can readily be seen from the above table that there was no decrease in the current to a stable low value. Such a decrease would be an indication of the channels being focused since at the time the proteins reach their pI, the conductivity decreases resulting in the low current. It is noted that pH of channel 6 did not stabilize even after operating for 210 mins. The relative protein concentration of each channel was measured by absorbance at 280 nm. It will also be seen from this table there was no stabilization of concentration in any of the channels.

EXAMPLE 2

In this example, the starting solution of Example 1 was desalted using an electrodialysis stack made by Ionics, Incorporated of Watertown, Mass. substantially as described in FIG. 1. The solution conductivity was reduced from 11.85 mS to 0.395 mS. 235 ml of this desalted protein mixture having albumin and hemoglobin concentrations as in Example 1 was then processed with the same recycling IEF apparatus keeping the power-input of 50 watts. The following Table II summarizes the results. Also, FIG. 2 shows the change of current as well as the pH of the three channels during the course of the run.

TABLE II

| Time Min. | Current M amp | pH in Efficient Channels | | | Relative Protein Concentration | | |
|---|---|---|---|---|---|---|---|
| | | 6 | 8 | 9 | 6 | 8 | 9 |
| 0 | 160 | 5.0 | 5.0 | 5.0 | 30.3 | 30.3 | 30.3 |

TABLE II-continued

| Time | Current | pH in Efficient Channels | | | Relative Protein Concentration | | |
|---|---|---|---|---|---|---|---|
| Min. | M amp | 6 | 8 | 9 | 6 | 8 | 9 |
| 30 | 25 | 5.2 | 7.5 | 11.1 | 35.9 | 38.3 | 10.8 |
| 60 | 10 | 5.2 | 7.5 | 7.5 | 20.3 | 29.7 | 29.4 |
| 90 | 5 | 5.0 | 7.3 | 7.5 | 20.7 | 28.9 | 24.6 |
| 120 | 5 | 4.7 | 7.4 | 7.5 | 20.6 | 28.9 | 27.9 |

It can be seen that the electrodialyzed sample focused much quicker than that of Example 1 with the current decreasing to 5 m amps in about 90 minutes. The pH's and absorbances of the channels were also stabilized in 90–120 minutes. Comparing these results with the non-electrodialyzed sample of Example 1, it is evident that the use of electrodialysis makes the subsequent process of electrofocusing much more efficient. The proteins attain their pI much quicker and form stable pH channels. Also a fairly stable protein concentration is obtained again indicating focused channels. Note also that albumin has been focused in channel 6 and hemoglobin focused in channels 8 and 9 as evident by the closeness of the channel pH's (at 120 min) to their pI's.

The above Examples 1 and 2 did not use ampholytes for the focusing step. In the following two examples use was made of ampholytes made by Bio-Rad Laboratories of Richmond, Calif. A concentration of 0.8% by volume of a 3–10 pH range ampholyte was used in the following two examples. The protein mixture comprised 0.4 wt./vol. percent each of purified human serum albumin, and hemoglobin. 235 ml of this solution were used in the following runs.

EXAMPLE 3

The solution of this example had a conductivity of 3.48 mS and electrodialysis was not employed. The following table summarizes the results after isoelectric focusing.

TABLE III

| Time | Current | pH in Effluent Channels | | | | Relative Protein Concentration | | | |
|---|---|---|---|---|---|---|---|---|---|
| Min. | M amps | 3 | 4 | 5 | 6 | 3 | 4 | 5 | 6 |
| 0 | 250 | 7.3 | 7.3 | 7.3 | 7.3 | 8.6 | 8.6 | 8.6 | 8.6 |
| 30 | 250 | 6.4 | 7.1 | 7.3 | 7.3 | 11.1 | 8.1 | 9.5 | 7.4 |
| 60 | 105 | 3.9 | 6.2 | 7.3 | 7.9 | 12.8 | 13.2 | 13.2 | 14.2 |
| 90 | 100 | 3.1 | 4.7 | 6.9 | 9.2 | 11.2 | 20.0 | 15.7 | 18.4 |
| 100 | 100 | 3.5 | 4.7 | 7.6 | 7.7 | 12.3 | 20.0 | 14.7 | 20.1 |

The above results show that the channel 4 which contains albumin was focused in about 90 minutes to a pI of 4.7. The protein concentrations also show it to be focused since there is no change from 90 minutes to 100 minutes reading. However channels 5 and 6 which were supposed to contain hemoglobin were still not focused to a pI of 7.4–7.5; also the protein concentrations had not stabilized in these channels even after 100 minutes.

EXAMPLE 4

In this example, the solution of Example 3 was desalted to a conductivity of 0.760 mS or about 22% of the original salt content by electrodialysis prior to subjecting to isoelectric focusing. The following table summarizes the results for three channels (3, 4 and 8) of pH close to the pI of the protein of interest (albumin pI=4.7 and hemoglobin pI=7.4).

TABLE IV

| Time | Current | pH Ineffluent | | | Relative Protein Concentration | | |
|---|---|---|---|---|---|---|---|
| Min. | M amps | 3 | 4 | 8 | 3 | 4 | 8 |
| 0 | 225 | 7.3 | 7.3 | 7.3 | 8.9 | 8.9 | 8.9 |
| 30 | 115 | 4.8 | 6.4 | 7.6 | 6.9 | 13.9 | 12.7 |
| 60 | 66 | 4.6 | 4.7 | 7.5 | 11.7 | 12.8 | 29.7 |
| 90 | 50 | 4.7 | 4.8 | 7.3 | 11.5 | 13.1 | 33.9 |

Thus the electrodialyzed sample attained fairly stable pI's and absorbances after 60 minutes of operation, with the next 30 minutes of operation showing insignificant changes in pH and absorbance. Albumin was found to be concentrated in channels 3 and 4 and hemoglobin in channel 8.

Comparing these results with those of Example 3, it becomes evident that the electrodialyzed samples focus quicker and stable concentrations and pI are reached in a shorter time.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

The embodiments of the invention in which an exclusive property or privilege is claimed are defined as follows:

1. Apparatus for the treatment of protein containing liquids comprising an electrodialysis membrane cell for desalting said liquids having substantially alternating desalting and concentrating chambers in combination with a isoelectric focusing membrane cell having substantially parallel channels with conduit means for passing the resulting desalted liquids from said electrodialysis cell into a reservoir and further conduit means for passing the said liquid to said channels of said isoelectric focusing cell.

2. The apparatus as claim 1 wherein the membranes of the electrodialysis cell comprise cation and anion permselective membranes arranged in alternating fashion within the said cell.

3. The apparatus of claim 1 wherein the membranes of said isoelectric focusing cell are electrically neutral microporous diffusion membranes arranged in a substantially parallel position within said cell.

4. The apparatus of claim 1 wherein means are provided for removing any turbidity present in said protein liquids prior to passage into said reservoir.

* * * * *